US00PP35935P2

(12) United States Plant Patent
Barnes

(10) Patent No.: US PP35,935 P2
(45) Date of Patent: Jul. 2, 2024

(54) ***VERBENA* PLANT NAMED 'WNVERSVPC24'**

(50) Latin Name: *Verbena hybrida*
Varietal Denomination: WNVERSVPC24

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/237,781

(22) Filed: Aug. 24, 2023

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Verbena* plant named 'WNVERSVPC24', characterized by its upright to outwardly spreading and mounding to trailing and decumbent plant habit; vigorous growth habit and rapid growth rate; freely branching habit; dark green-colored leaves; freely flowering habit; large inflorescences with large purplish pink-colored flowers that are held above and beyond the foliar plane; and resistance to Powdery Mildew.

2 Drawing Sheets

Figure 1:
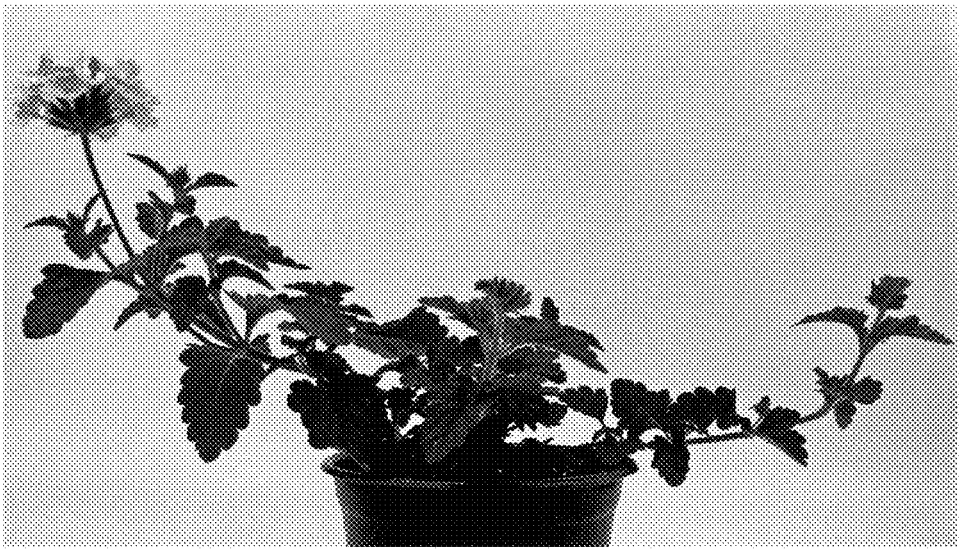

Botanical designation: *Verbena hybrida.*
Cultivar denomination: 'WNVERSVPC24'.

BACKGROUND OF THE INVENTION

The present invention relates to a new and distinct cultivar of *Verbena* plant, botanically known as *Verbena hybrida* and hereinafter referred to by the name 'WNVERSVPC24'.

The new *Verbena* plant is a product of a planned breeding program conducted by the Inventor in Bonsall, California. The objective of the breeding program is to create new vigorous and freely-branching *Verbena* plants with numerous large flowers and good container and garden performance.

The new *Verbena* plant originated from a cross-pollination made by the Inventor on Sep. 24, 2019 in Bonsall, California of *Verbena hybrida* 'RIKAV17805', disclosed in U.S. Plant Pat. No. 25,394, as the female, or seed, parent with a proprietary selection of *Verbena hybrida* identified as code number 18VB006-01, not patented, as the male, or pollen, parent. The new *Verbena* plant was discovered and selected by the Inventor as a single flowering plant from within the progeny of the stated cross-pollination in a controlled greenhouse environment in Bonsall, California on Jun. 1, 2020.

Asexual reproduction of the new *Verbena* plant by vegetative terminal cuttings in a controlled environment in Bonsall, California since Jun. 3, 2020, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNVERSVPC24'. These characteristics in combination distinguish 'WNVERSVPC24' as a new and distinct *Verbena* plant:

1. Upright to outwardly spreading and mounding to trailing and decumbent plant habit.
2. Vigorous growth habit and rapid growth rate.
3. Freely branching habit.
4. Dark green-colored leaves.
5. Freely flowering habit.
6. Large inflorescences with large purplish pink-colored flowers that are held above and beyond the foliar plane.
7. Resistance to Powdery Mildew (*Podosphaera xanthii*).

Plants of the new *Verbena* can be compared to plants of the female parent, 'RIKAV17805'. Plants of the new *Verbena* differ primarily from plants of 'RIKAV17805' in the following characteristics:

1. Plants of the new *Verbena* are more vigorous than plants of 'RIKAV17805'.
2. Plants of the new *Verbena* have larger inflorescences and larger flowers than plants of 'RIKAV17805'.
3. Flowers of plants of the new *Verbena* are purplish pink in color whereas flowers of plants of 'RIKAV17805' are pure white in color.
4. Plants of the new *Verbena* are more resistant to Powdery Mildew than plants of 'RIKAV17805'.

Plants of the new *Verbena* can be compared to plants of the male parent selection. Plants of the new *Verbena* differ primarily from plants of the male parent selection in the following characteristics:

1. Plants of the new *Verbena* are more freely branching and denser than plants of the male parent selection.

2. Plants of the new *Verbena* have purplish pink-colored flowers whereas plants of the male parent selection have violet purple-colored flowers.

Plants of the new *Verbena* can be compared to plants of the *Verbena hybrida* 'RIKAV18302', disclosed in U.S. Plant Pat. No. 25,396. In side-by-side comparisons, plants of the new *Verbena* differ primarily from plants of 'RIKAV18302' in the following characteristics:

1. Plants of the new *Verbena* are more vigorous than plants of 'RIKAV18302'.
2. Plants of the new *Verbena* have purplish pink-colored flowers whereas plants of 'RIKAV18302' have dark violet-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph on the first sheet (FIG. 1) is a side perspective view of a typical flowering plant of 'WNVERSVPC24' grown in a container.

Figure 2:
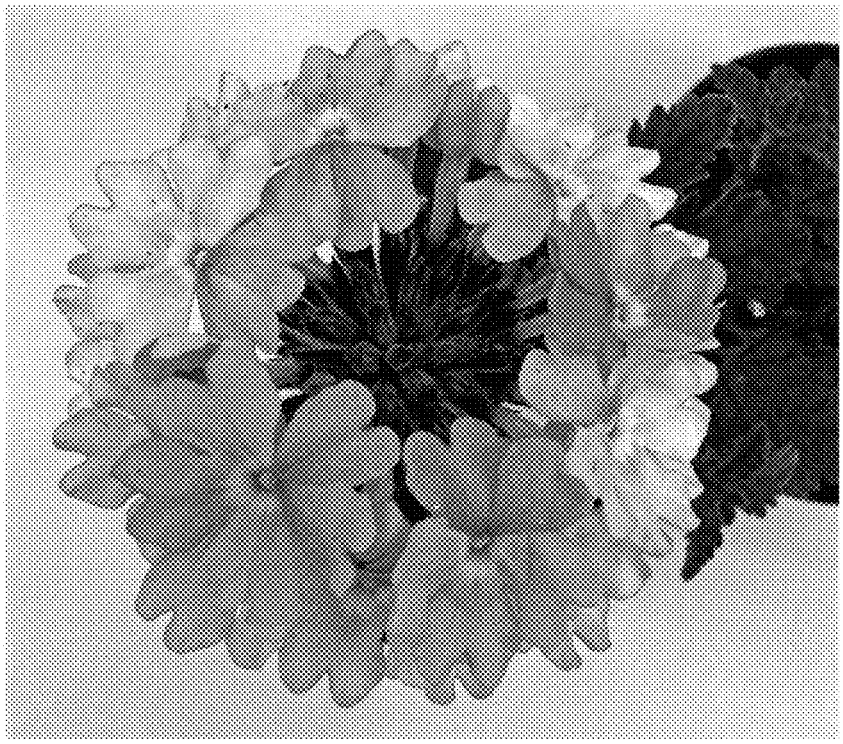

The photograph on the second sheet (FIG. 2) is a close-up view of a typical inflorescence of 'WNVERSVPC24'.

DETAILED BOTANICAL DESCRIPTION

The aforementioned photographs and following observations and measurements describe plants grown during the spring in 723 ml containers in a glass-covered greenhouse in Loudon, New Hampshire and under cultural practices typical of commercial *Verbena* production. During the production of the plants, day and night temperatures averaged 20 C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Verbena hybrida* 'WNVERSVPC24'.

Parentage:

*Female, or seed, parent.*—*Verbena hybrida* 'RIKAV17805', disclosed in U.S. Plant Pat. No. 25,394.

*Male, or pollen, parent.*—Proprietary seedling selection of *Verbena hybrida* identified as code number 18VB006-01, not patented.

Propagation:

*Type cutting.*—Vegetative terminal cuttings.

*Time to initiate roots, summer.*—About three days at temperatures ranging from about 16 C to 29 C.

*Time to initiate roots, winter.*—About four days at temperatures ranging from about 16 C to 21 C.

*Time to produce a rooted plant, summer.*—About 15 days at temperatures ranging from about 16 C to 29 C.

*Time to produce a rooted plant, winter.*—About 20 days at temperatures ranging from about 16 C to 21 C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding to trailing and decumbent plant habit; freely branching habit with lateral branches potentially developing at every node, pinching enhances branching potential; dense and bushy plant habit; vigorous growth habit and rapid growth rate.

*Plant height.*—About 18 cm to 20 cm.

*Plant diameter (spread).*—About 36 cm to 45 cm.

Lateral branch description:

*Length.*—About 29 cm.

*Diameter.*—About 3.75 mm to 4 mm.

*Internode length.*—About 3.5 cm.

*Orientation.*—Initially upright then outwardly spreading to trailing and decumbent.

*Strength.*—Strong; flexible.

*Texture and luster.*—Densely pubescent; slightly glossy; becoming woody with subsequent development.

*Color, developing.*—Close to 144A.

*Color, developed.*—Close to 146A; if woody, close to 199A.

Leaf description:

*Arrangement.*—Opposite, simple.

*Length.*—About 7.2 cm.

*Width.*—About 4.5 cm to 5 cm.

*Shape.*—Deltoid, elongated.

*Apex.*—Acute.

*Base.*—Truncate.

*Margin.*—Crenate to dentate.

*Texture and luster, upper surface.*—Moderately pubescent, rough; glossy.

*Texture and luster, lower surface.*—Mostly glabrous with pubescence along veins and margins; slightly glossy.

*Venation pattern.*—Pinnate.

*Color.*—Developing leaves, upper surface: Close to 147A. Developing leaves, lower surface: More green than 147B. Fully expanded leaves, upper surface: Close to 147A; venation, close to 146A. Fully expanded leaves, lower surface: Close to 147B; venation, close to 146A to 146B.

*Petioles.*—Length: About 1.5 cm. Diameter: About 3 mm. Strength: Strong; flexible. Texture and luster, upper and lower surfaces: Densely pubescent; slightly glossy. Color, upper surface: Close to 144B. Color, lower surface: Close to between 146B and 144B.

Flower description:

*Flower arrangement and habit.*—Sessile salverform flowers arranged in upright hemispherical terminal corymbs; flowers face upward or outwardly depending on the position in the inflorescence; freely flowering habit with about 28 flowers developing per inflorescence; inflorescences potentially forming at every node and numerous inflorescences developing per plant during the flowering season.

*Natural flowering season.*—Plants flower continuously from spring until the autumn; early flowering habit, plants begin flowering about five to six weeks after planting.

*Flower longevity*.—Flowers last about five to seven days on the plant; flowers not persistent.

*Fragrance*.—None detected.

*Inflorescence height*.—About 5 cm.

*Inflorescence diameter*.—About 6.8 cm.

*Inflorescence buds*.—Length: About 1.5 cm. Diameter: About 1.2 cm. Shape: Somewhat conical. Texture and luster: Pubescent; glossy. Color: Close to 146A.

*Flower buds*.—Length: About 1.5 cm. Diameter: About 2.5 mm. Shape: Elongated oblong, tubular. Texture and luster: Pubescent; slightly glossy. Color: Close to 146A.

*Flower diameter*.—About 2.3 cm.

*Flower depth* (*height*).—About 2.5 cm.

*Throat diameter*.—About 2 mm.

*Tube length*.—About 2 cm.

*Tube diameter, proximally*.—About 1.5 mm.

*Corolla*.—Arrangement: Single whorl of five fused petals fused towards the base into a slender narrow tube. Petal lobe length: About 1 cm. Petal lobe width: About 9 mm. Petal lobe shape: Cordate. Petal lobe apex: Retuse. Petal margin: Entire; slightly undulate. Petal texture and luster, upper surface: Smooth, glabrous; velvety; matte. Petal texture and luster, lower surface: Smooth, glabrous; matte. Throat texture and luster: Slightly pubescent; matte. Tube texture and luster: Slightly pubescent; matte. Color: Petal lobes, when opening and fully opened, upper surface: Close to 68A to 68B becoming close to 68C to 68D and eventually closer to 65C to 65D with subsequent development; venation, similar to lamina colors. Petal lobes, when opening and fully opened, lower surface: Close to 69A becoming closer to 69C with subsequent development; venation, similar to lamina colors. Throat: Close to 157C to 157D; venation, close to 79A. Tube: Close to 145D; venation, close to 145D.

*Calyx*.—Arrangement: Single whorl of five fused sepals fused towards the base into a slender tube. Length: About 1.5 cm. Diameter: About 3 mm. Sepal length: About 1.5 cm. Sepal width: About 1 mm. Sepal shape: Acicular. Sepal apex: Acuminate. Sepal margin: Entire. Sepal texture and luster, upper surface: Pubescent; slightly glossy. Sepal texture and luster, lower surface: Pubescent; moderately glossy. Sepal color, upper and lower surfaces: Close to 146A.

*Peduncles*.—Length: About 2.5 cm to 4 cm. Diameter: About 2.5 mm. Strength: Strong; flexible, wiry. Aspect: Mostly upright. Texture and luster: Densely pubescent; slightly glossy. Color: Close to 144A.

*Reproductive organs*.—Stamens: Quantity and arrangement: Five per flower, filaments partially adnate to corolla tube. Filament length: About 1.5 cm. Filament color: Close to 145D. Anther size: About 0.75 mm by 1 mm. Anther shape: Oblong. Anther color: Close to 154A. Pollen amount: None observed. Pistils: Quantity: One per flower. Pistil length: About 1.2 cm. Stigma shape: Bi-parted. Stigma diameter: About 1 mm. Stigma color: Close to 144A. Style length: About 1 cm. Style color: Close to 145D. Ovary color: Close to 144A. Fruits and seeds: To date, fruit and seed development have not been observed on plants of the new *Verbena*.

Temperature tolerance: Plants of the new *Verbena* have been observed to tolerate temperatures from about 2 C to about 40 C and are suitable for USDA Hardiness Zones 8a to 11b.

Pathogen & pest resistance: Plants of the new *Verbena* have been observed to be resistant to Powdery Mildew (*Podosphaera xanthii*). To date, plants of the new *Verbena* have not been observed to be resistant to pests and other pathogens common to *Verbena* plants.

It is claimed:

1. A new and distinct *Verbena* plant named 'WNVERSVPC24' as illustrated and described.

* * * * *